United States Patent [19]

Aysta et al.

[11] Patent Number: 5,032,131
[45] Date of Patent: Jul. 16, 1991

[54] PROSTHESIS HOLDING DEVICE

[75] Inventors: James E. Aysta, Stillwater; John T. Capecchi, Oakdale, both of Minn.; Carl Franzblau, Newton, Mass.; Donald F. Gibbons, North Oaks, Minn.; Randall L. Knoll, Mahtomedi, Minn.; Howard M. Leibowitz, Weston, Mass.; Vickery Trinkaus-Randall, Maynard, Mass.

[73] Assignee: Minnesota Mining and Manufacturing Company, St. Paul, Minn.

[21] Appl. No.: 163,515

[22] Filed: Mar. 2, 1988

[51] Int. Cl.[5] ............................................. C12N 5/00
[52] U.S. Cl. ......................................... 623/66; 435/1; 435/240.23
[58] Field of Search ................. 435/1, 240.23; 623/66, 623/65

[56] References Cited

U.S. PATENT DOCUMENTS

| 4,205,747 | 6/1980 | Gilliam et al. | 206/5.1 |
| 4,299,919 | 11/1981 | Jellinek | 435-1 |
| 4,688,387 | 8/1987 | Conaway | 435-1 |
| 4,762,794 | 8/1988 | Nees | 435-1 |

FOREIGN PATENT DOCUMENTS 0262766 7/1987 European Pat. Off. .

Primary Examiner—Barry S. Richman
Assistant Examiner—T. J. Wallen
Attorney, Agent, or Firm—Fish & Richardson

[57] ABSTRACT

A holding device for seeding cells on a surface of a prosthesis including chamber means for partially defining a first chamber with the first surface, and sealing means for providing a seal between the chamber means and the prosthesis so as to isolate the seeding surface from another portion of the prosthesis.

12 Claims, 1 Drawing Sheet

PROSTHESIS HOLDING DEVICE

BACKGROUND OF THE INVENTION

The invention relates to a device for holding a prosthesis, e.g., a corneal prosthesis.

A synthetic implant is a synthetic material member incorporated into a living body, typically replacing or assisting a failing living component. To be successful it must serve its intended purpose and not be rejected by the receiving body or otherwise have unacceptable side effects.

A corneal prosthesis, often referred to as a keratoprosthesis, replaces part or all of the cornea, typically when the cornea has been damaged so as to cease serving the function of an optically transparent window to the retina. A complication to be avoided with a corneal prosthesis is extrusion of the prosthesis from the eye when epithelial tissue grows in behind the prosthesis.

It may be desirable to seed a prosthesis with cells prior to implantation to facilitate adherence and growth of cells thereon or therein when implanted.

SUMMARY OF THE INVENTION

Our invention features in general a holding device for holding a prosthesis while it is being treated (e.g., seeded) prior to implantation. The device has a first chamber means that partially defines a first treating chamber with a surface of the prosthesis. The device also has means providing a seal between the first chamber means and the prosthesis so as to isolate the surface from another portion of the prosthesis, thus permitting treating at only a portion of the prosthesis.

In preferred embodiments a second chamber means is used to isolate a second surface from the first, permitting seeding of one type of cell on one surface and another type of cell on another surface; the prosthesis is generally flat (it is lens shaped and has a slight curvature), and its two seeding surfaces are on opposite sides of the prosthesis; the chamber means are provided by cylindrical housings, and the seals are O-rings received in opposing annular recesses of the housings; the housings are secured together by an annular collar; the housings have open ends that are sealed shut by caps; ports are provided to flush nutrient medium through a seeding chamber; a tube that communicates with a seeding chamber extends upwardly to a height above the height of the prosthesis to maintain liquid level; tubes could optionally be fitted with a semipermeable membrane that seals out contaminants but allows gas exchange.

Other features and advantages of the invention will be apparent from the following description of a preferred embodiment thereof and from the claims.

DESCRIPTION OF THE PREFERRED EMBODIMENT OF THE INVENTION

The preferred embodiment of the invention will now be described.

DRAWINGS

STRUCTURE

Figure 1:
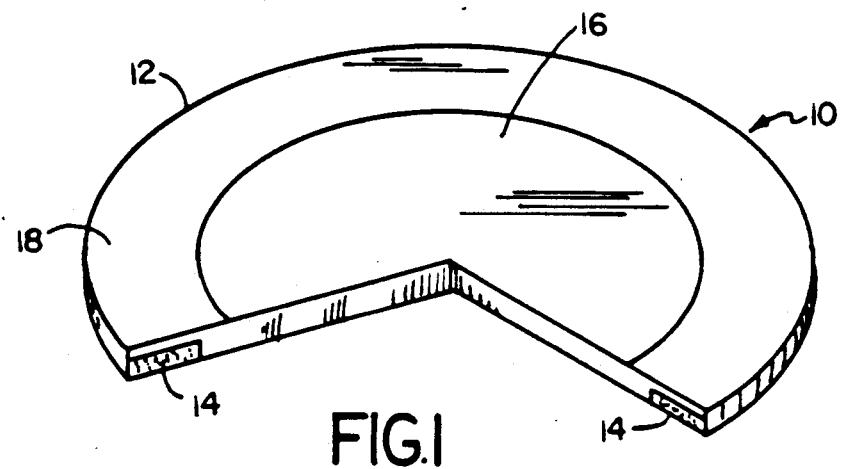
FIG. 1 is a diagrammatic perspective view, partially broken away, of a corneal prosthesis.

Referring to FIG. 1, there is shown corneal prosthesis 10 including optical element 12 and porous outer skirt 14. Prosthesis 10, described as generally flat, is defined by two spherical surfaces separated by a fixed distance. Optical element 12 includes a full-depth optically transparent central portion 16 and a thinner outer portion 18 that overlies skirt 14, which extends around the periphery of prosthesis 10. The material of optical element 16 preferably is a hydrogel, e.g., made of a polyvinyl alcohol copolymer system, as described in Ofstead U.S. Pat. No. 4,618,649 ("Ofstead '649") and Ofstead U.S. Pat. No. 4,528,325 (Ofstead '325), preferably polyvinyl-alcohol-co vinyl acetate 97.6:2.4 mole percent (prepared from a copolymer of vinyltrifluoroacetate and vinyl acetate) made according to the methods described in Ofstead '649 (Example 8). Porous outer skirt 14 is preferably made of a coherent mass of melt blown polybutylene fibers having an interconnected network of pores. The majority of fibers are preferably between 2 and 20 microns in diameter, and the majority of pores are preferably between 10 and 100 microns.

Figure 2:
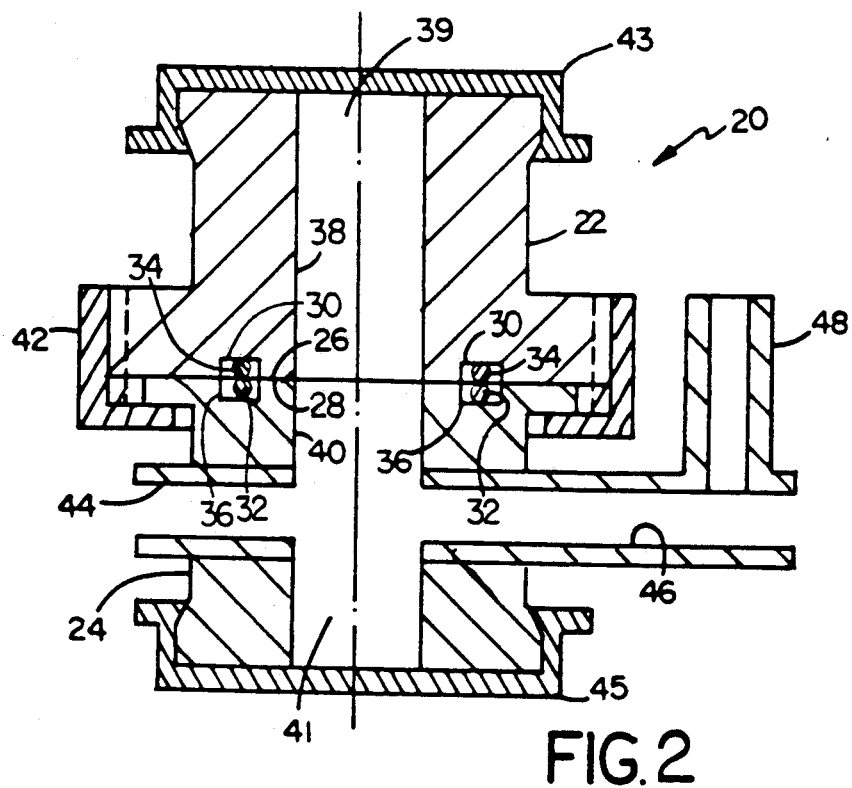
FIG. 2 is a diagrammatic vertical sectional view of a holding device used to hold the FIG. 1 prosthesis during seeding according to the invention.

Referring to FIG. 2, there is shown holding device 20 used for holding prosthesis 10 while seeding different cells on different surfaces of corneal prosthesis 10. Upper and lower housings 22, 24 mate at flat surfaces 26, 28, in which are provided opposing annular recesses 30, 32, retaining opposing O-rings 34, 36 therein. Housing 22 has a cylindrical bore 38 to provide a first seeding chamber 39, and housing 24 similarly has cylindrical bore 40 to provide a second seeding chamber 41. Housings 22, 24 are secured together by threaded collar 42, and ar sealed closed at their respective ends by snap-on caps 43, 45. Lower housing 24 has ports 44, 46, the latter communicating with upwardly directed tube 48.

Use

Prior to implantation of prosthesis 10 in the patient's eye, holding device 20 is used to seed the anterior surface of optical element 12 with epithelial cells and porous skirt 14 with stromal keratocytes. The completed prosthesis 10, shown in FIG. 1, has an outer diameter equal to that of bores 38, 40. Prior to seeding, prosthesis 10 initially has a skirt 14 and overlying portion 18 that extend beyond the bore diameters to slightly more than the diameter of O-rings 34, 36 so that the upper surface of completed prosthesis 10 is sealably isolated from the lower surface. The oversized prosthesis is sealed between O-rings 34, 36, with the anterior surface forming second seeding chamber 41 with bore 40 and the posterior surface forming first seeding chamber 39 with bore 38. Device 20 is filled with culture medium in chamber 39 in bore 38, sealed closed, and placed in a position inverted from that of FIG. 2, and culture medium with epithelial cells is added to chamber 41. After epithelial cell attachment to the anterior surface of optical element 12, device 20 is inverted to the position of FIG. 2, and stromal keratocytes are added to chamber 39. Prior to seeding, both optical element 12 and porous skirt 14 can optionally be coated with a basement membrane component to facilitate attachment and healing when implanted; one or more of the following could be used: laminin, fibronectin, Type I collagen, Type IV collagen or a cell-free extract prepared from the extracellular matrix of corneal epithelial cells.

During seeding of the porous skirt, culture medium can be flushed through ports 44, 46 to maintain the epithelial cells. Tube 48 maintains the liquid level in chamber 41 so that the nutrient medium is in contact with the prosthesis. The first seeding chamber 39 in bore 38 might additionally be provided with a cylindrical barrier (not shown) to keep the stromal keratocytes at the porous outer skirt only and away from the posterior surface of central portion 16. After seeding has been completed, caps 43, 45 are removed, and prosthesis 10 and holding device 20 are transferred under sterile conditions to a sterile punch in which prosthesis 10 is cut from the seeded, oversized prosthesis. The sterile punch could use bore 38 for alignment, and a backing plug could be inserted in bore 40 to assist punching out the proper size prosthesis. Device 20 advantageously prevents cross-contamination of the cell types, keeping the epithelium from populating the porous skirt, something which would lead to epithelial growth under the prosthesis and extrusion.

Other Embodiments

Other embodiments of the invention are within the scope of the following claims. For example, the two seeding surfaces might be on the same side of a prosthesis, and the prosthesis might not be generally flat. Also other chamber shapes could be used, and other sealing means could be used. Also, other means of maintaining appropriate culture conditions in the lower chamber once seeded could be used, and the order of cell seeding could be reversed. Finally, in addition to seeding, holder 20 might have utility, e.g., in treating (e.g., chemically) only one surface of an object while isolating another portion.

What is claimed is:

1. The combination comprising
  a prosthesis having a first treating surface to be treated in a manner that changes the physical characteristics of said surface by contact with a first treatment liquid and another surface portion to be prevented from contacting said first treatment liquid, and
  a holding device for holding said prosthesis while treating said first treating surface of said prosthesis, said holding device comprising
  first chamber means for partially defining a first treating chamber with said first treating surface,
  said first chamber means including one or more first walls that partially surround said first treating chamber and that end at a first opening, and
  sealing means for providing a seal between said first chamber means and the prosthesis so as to isolate said first treating surface from said another portion of said prosthesis,
  said sealing means including a member providing a first sealing surface that surrounds said first opening and is sealed to said one or more first walls around said first opening and makes sealing contact with said prosthesis around said first treating surface,
  whereby said first treating chamber is formed for receiving and containing said first treatment liquid for treating said first treating surface, and said another surface portion is prevented from contacting said first treatment liquid.

2. The device of claim 1 wherein said prosthesis has a second treating surface to be treated in a manner that changes the physical characteristics of said second treating surface by contact with a second treatment liquid, and further comprising a second chamber means for partially defining a second treating chamber, said second chamber means including one or more second walls that partially surround said second treating chamber and end at an opening, said sealing means including means for isolating said first treating surface from said second treating surface,
  said sealing means including a second member providing a second sealing surface that surrounds said second opening and is sealed to said second walls around said second opening and makes sealing contact with said prosthesis around said second treating surface.

3. The device of claim 2 wherein said prosthesis is generally flat, said first and second treating surfaces are on opposite sides of said prosthesis, and said first and second chamber means comprise housings having facing end surfaces for engaging said prosthesis therebetween.

4. The device of claim 3 wherein said first and second housings are cylindrical in shape, and said sealing means comprises opposing O-rings located in opposing recesses of said end surfaces, said first and second sealing surfaces being provided by respective said O-rings.

5. The device of claim 3 further comprising an outer collar releasably securing said first housing to said second housing.

6. The device of claim 3 further comprising a tube that communicates with said first chamber and extends to a height higher than said prosthesis so as to maintain liquid level.

7. The device of claim 3 further comprising a tube that communicates with said first chamber, extends to a height higher than said prosthesis, and is capped with a self-sealing, gas permeable membrane so as to maintain liquid level, allow maintenance of proper gas levels, and seal out contaminants.

8. The method of claim 2 wherein said prosthesis is generally flat, said first and second treating surfaces are on opposite sides of said prosthesis.

9. The device of claim 1 wherein said first chamber means comprises ports to said first chamber.

10. The device of claim 1 further comprising a self-aligning punch having an outer surface shape similar to that of an inner surface of said first chamber so as to be adapted to punch said prosthesis.

11. A method of treating a prosthesis comprising
  providing a prosthesis having a first treating surface to be treated in a manner that changes the physical characteristics of said surface by contact with a first treatment liquid and another surface portion to be prevented from contacting said first treatment liquid,
  providing a holding device having first chamber means for partially defining a first treating chamber with said first treating surface,
  said first chamber means including one or more first walls that partially surround said first treating chamber and that end at a first opening,
  said holding device including a sealing means including a member providing a first sealing surface that surrounds said first opening and is sealed to said walls around said first opening and makes sealing contact with said prosthesis around said first treating surface,
  holding said prosthesis in said holder,
  partially defining said first chamber with said first chamber means and said prosthesis, sealing between said prosthesis and said first chamber means, and treating said first treating surface while said first treating surface is isolated from said another portion, said treating including providing and containing said first treatment liquid in said first treating chamber while said another surface portion is prevented from contacting said first treatment liquid.

12. The method of claim 11 wherein said prosthesis has a second treating surface to be treated in a manner that changes the physical characteristics of said second surface of contact with a second treatment liquid and further comprising isolating said first treating surface from said second treating surface while treating said first and second surfaces by contacting them with respective treatment liquids.

* * * * *